United States Patent
Plos et al.

(10) Patent No.: US 7,179,305 B2
(45) Date of Patent: Feb. 20, 2007

(54) PROCESS FOR DYEING KERATIN FIBERS WITH NINHYDRIN COMPOUNDS COMPRISING ONE OR MORE FUSED RINGS

(75) Inventors: Grégory Plos, Tokyo (JP); Luc Gourlaouen, Asnieres (FR)

(73) Assignee: L'Oreal S.A., Paris (FR)

( * ) Notice: Subject to any disclaimer, the term of this patent is extended or adjusted under 35 U.S.C. 154(b) by 387 days.

(21) Appl. No.: 10/898,368

(22) Filed: Jul. 26, 2004

(65) Prior Publication Data

US 2005/0050653 A1    Mar. 10, 2005

Related U.S. Application Data

(60) Provisional application No. 60/499,456, filed on Sep. 3, 2003.

(30) Foreign Application Priority Data

Jul. 25, 2003 (FR) .................... 03 09176
Mar. 4, 2004 (FR) .................... 04 02245

(51) Int. Cl.
*A61K 7/13* (2006.01)
(52) U.S. Cl. .............. 8/405; 8/406; 8/407; 8/410; 8/411; 8/421; 8/607; 568/327
(58) Field of Classification Search .............. 8/405, 8/406, 407, 410, 411, 421, 607; 568/327
See application file for complete search history.

(56) References Cited

FOREIGN PATENT DOCUMENTS

DE    43 17 855 A    12/1994
DE    4317855 A1 *   12/1994

OTHER PUBLICATIONS

English Abstract of the Patent No. DE 4317855 A1.*
STIC Search Report (Aug. 4, 2006).*
Database WPI, Derwent Publications Ltd., London, GB; AN 1973-22659U, XP002285499.
English language Derwent Abstract of DE 43 17 855 A, Dec. 1, 1994.

* cited by examiner

*Primary Examiner*—Eisa Elhilo
(74) *Attorney, Agent, or Firm*—Finnegan, Henderson, Farabow, Garrett & Dunner, L.L.P.

(57) ABSTRACT

Disclosed are processes and compositions for dyeing keratin materials comprising, in a medium that is suitable for dyeing, at least one ninhydrin compound of formula (I)

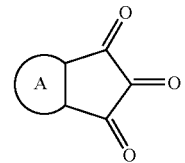

(I)

wherein,

A comprises an at least 12-membered polycycle, such as those chosen from anthracenyl, tetracenyl, phenanthrenyl, and azulenyl groups. Hair dyeing processes and kits using these compositions are also disclosed.

24 Claims, No Drawings

PROCESS FOR DYEING KERATIN FIBERS WITH NINHYDRIN COMPOUNDS COMPRISING ONE OR MORE FUSED RINGS

This application claims benefit of domestic priority to U.S. Provisional Application No. 60/499,456, filed Sep. 3, 2003, which is herein incorporated by reference.

The present disclosure relates to processes and compositions for dyeing keratin materials, such as hair dye compositions, comprising at least one ninhydrin compound comprising one or more fused rings, which may be combined with a compound comprising a primary or secondary amine function or a compound comprising an activated methylene function. The present disclosure also relates to a dyeing process using such compositions and to a multi-component coloring agent for performing such a process.

Many people wish, and have done for a long time, to modify the color of their skin, their eyelashes or their hair, for example, to mask their grey hair. Several techniques have been developed to do this.

For example, it is known practice to dye human keratin fibers, such as the hair, with dye compositions comprising oxidation dye precursors, which are generally known as oxidation bases. These oxidation bases are colorless or weakly colored compounds which, when combined with oxidizing products, give rise to colored compounds by a process of oxidative condensation. These dyes are insoluble and are trapped inside the hair fiber.

It is also known that the shades obtained with these oxidation bases can be varied by combining them with couplers or coloration modifiers. The variety of molecules used as oxidation bases and couplers allows a wide range of colors to be obtained.

The colorations obtained show good shampoo-fastness. However, the oxidation reaction takes place using oxidizing products such as an aqueous hydrogen peroxide solution in basic medium. These oxidizing agents attack the keratin of the hair, resulting in cosmetic and mechanical properties that may become greatly degraded in the case of repeated colorations.

It is also known practice to dye human keratin fibers by direct dyeing, which comprises applying to the keratin fibers direct dyes, which are colored and coloring molecules that have affinity for the fibers. Examples of direct dyes conventionally used that may be mentioned include nitro dyes, benzene dyes, anthraquinone dyes, nitropyridine dyes, azo dyes, cationic azo dyes, xanthene dyes, acridine dyes, azine dyes, triarylmethane dyes or natural dyes.

Although the colorations thus obtained are certainly very chromatic and do not cause any chemical degradation of keratin, they have the drawback of being only temporary or semi-permanent, for example, fading out at best after only 4 to 5 shampoo washes.

There is consequently still a need for dyeing systems and processes that can give fast results without involving the use of oxidizing agents liable to degrade the keratin materials.

The Inventor has discovered, surprisingly, that the use of ninhydrin compounds comprising one or more fused rings and described in greater detail hereinbelow makes it possible to dye keratin fibers, such as the hair, with fastness equivalent to or greater than that obtained by oxidation dyeing, and in the absence of strong oxidizing agents, thus keeping the keratin materials perfectly intact.

The ninhydrin compounds mentioned above can be used in combination with compounds comprising labile hydrogen, such as primary or secondary amines or compounds comprising an activated methylene function.

The colorations thus obtained show good chromaticities and are distinguished in particular by excellent wash-fastness (several tens of shampoo washes).

Accordingly, disclosed herein is a process for dyeing keratin materials comprising, applying to keratin materials a composition comprising, in a medium that is suitable for dyeing, at least one compound of formula (I) or the tautomer thereof:

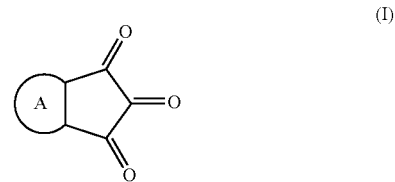

wherein,

A comprises an at least 12-membered fused aromatic polycycle.

In one embodiment, the group A may be chosen from anthracenyl, tetracenyl, phenanthrenyl and azulenyl groups.

The group A may also be substituted with groups chosen from halo groups, such as chloro, iodo, bromo and fluoro, $C_1$–$C_6$ alkyl groups, hydroxyl groups, $C_1$–$C_6$ alkoxy groups, amino groups, mono- and di($C_1$–$C_6$ alkyl)amino groups, mono- and dihydroxy($C_1$–$C_6$ alkyl)amino groups, tri($C_1$–$C_6$ alkyl)ammonio groups, imidazolyl groups, pyridyl groups, thio groups, ($C_1$–$C_6$ alkyl)thio groups, thio($C_1$–$C_6$ alkyl) groups, ($C_1$–$C_6$ alkyl)carbonyl groups, hydrogenocarbonyl groups, hydroxycarbonyl groups, ($C_1$–$C_6$ alkoxy)carbonyl groups, nitro groups and sulphonato groups, and the corresponding protonated groups such as ammonio, imidazolio and pyridinio.

Such compositions are useful for dyeing keratin fibers, such as the hair.

The compounds of formula (I) may also include, for example, the corresponding addition salts with acids and addition salts with bases.

The ninhydrin compounds of formula (I) above are used in the present invention in a cosmetically acceptable medium generally containing a large fraction of water. When they are dissolved in such an aqueous medium, the ninhydrin compounds of formula (I) are in hydration equilibrium with the gem-diol (or carbonyl hydrate) form corresponding to formula (Ia) below:

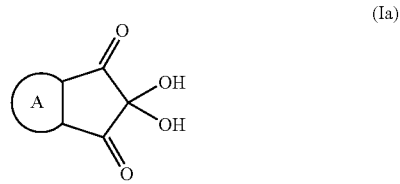

When reference is made to ninhydrin compounds of formula (I) in the present disclosure, they comprise not only the compounds of formula (I) but also the corresponding hydrated forms of formula (Ia).

The ninhydrin compounds described herein include derivatives of such compounds. Non-limiting examples of ninhydrin derivatives that may be used in accordance with the present disclosure for dyeing keratin fibers include the following:

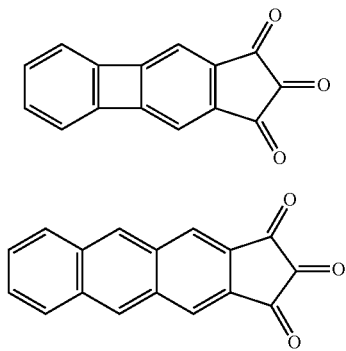

The ninhydrin compounds used in the present disclosure are known. For example, the synthesis of the above ninhydrin compounds (a) and (b) is described in the following publications:

(a): Buckland P. R., McOmie J. F. W., Biphenylenes XXIX synthesis of cyclobuta[b]biphenylene-1-carboxylic acid and of cyclopenteno[b]biphenylene-1,2,3-trione, Tetrahedron, 1977, 33, 1797–1801; and (b) Hallman J. L., Bartsch R. A., Synthesis of naphtha [f]ninhydrin, J. Org. Chem. 1991, 56, 6243–6245.

In accordance with the present disclosure, the ninhydrin compounds of formula (I) described above may be used alone for dyeing keratin materials. One reason for this is that these compounds are capable of generating colored molecules with the amine functions of keratin (colored reaction).

Compounds of formula (I) may also be used in combination with at least one activator, which makes it possible to modify the reaction kinetics of the ninhydrin compound with the keratin material. Such an activator may be chosen from an oxidizing agent, a reducing agent, Brönstedt acids, a metal catalyst including catalysts based on a transition metal such as iron, platinum or palladium, proteins, and enzymes, compounds that modify the ionic strength of the medium, such as NaCl salts, compounds comprising labile hydrogen chosen from those comprising a primary or secondary amine function and those comprising an activated methylene function. A mixture of such compounds may also be used.

The compounds comprising a primary amine or secondary amine function include aromatic amines.

Examples of such aromatic amines that may be mentioned include N,N-dimethyl-p-phenylenediamine, N,N-diethyl-p-phenylenediamine, N-(2-hydroxyethyl)-N-ethyl-p-phenylenediamine, N,N,-bis(2-hydroxyethyl)-p-phenylenediamine, N-(2-methoxyethyl)-p-phenylenediamine, 2,3-, 2,4- or 2,5-dichloro-p-phenylenediamine, 2-chloro-p-phenylenediamine, 2,5-dihydroxy-4-morpholinoaniline dihydrobromide, 2-, 3- or 4-aminophenol, 2-aminomethyl4-aminophenol, 2-hydroxymethyl-4-aminophenol, ortho-phenylenediamine, p-phenylenediamine, ortho-toluenediamine, 2,5-diaminotoluene, 2,5-diaminophenol, 2,5-diaminophenethol, 4-amino-3-methylphenol, 2-(2,5-diaminophenyl)ethanol, 2,4-diaminophenoxyethanol, 2-(2,5-diaminophenoxy)ethanol, 4-methylaminoaniline, 3-amino-4-(2'-hydroxyethyloxy)aniline, 3,4-methylenediaminoaniline, 3,4-methylenedioxyaniline, 3-amino-2,4-dichlorophenol, 4-methylaminophenol, 2-methyl-5-aminophenol, 3-methyl4-aminophenol, 2-methyl-5-(2-hydroxyethylamino)phenol, 6-methyl-3-amino-2-chlorophenol, 2-methyl-5-amino-4-chlorophenol, 3,4-methylene-dioxyphenol, 5-(2-hydroxyethylamino)-4-methoxy-2-methylphenol, 4-amino-2-hydroxymethylphenol, 1,3-diamino-2,4-dimethoxybenzene, 2-, 3- or 4-aminobenzoic acid, 2-amino-, 3-amino- or 4-aminophenylacetic acid, 2,3-, 2,4-, 2,5-, 3,4- or 3,5-diaminobenzoic acid, 4-amino- or 5-aminosalicylic acid, 3-amino-4-hydroxybenzoic acid, 4-amino-3-hydroxybenzoic acid, 2-amino, 3-amino- or 4-aminobenzenesulphonic acid, 3-amino-4-hydroxybenzenesulphonic acid, 4-amino-3-hydroxynaphthalene-1-sulphonic acid, 6-amino-7-hydroxynaphthalene-2-sulphonic acid, 7-amino-4-hydroxynaphthalene-2-sulphonic acid, 4-amino-5-hydroxynaphthalene-2, 7-disulphonic acid, 3-amino-2-naphthoic acid, 3-aminophthalic acid, 5-aminoisophthalic acid, 1,3,5-triaminobenzene, 1,2,4-triaminobenzene, 1,2,4,5-tetraaminobenzene, 2,4,5-triaminophenol, pentaaminobenzene, hexaaminobenzene, 2,4,6-triaminoresorcinol, 4,5-diaminopyrocatechol, 4,6-diaminopyrogallol, 3,5-diamino-4-hydroxypyrocatechol, and aromatic anilines and aromatic phenols comprising another aromatic residue, of formula (II)

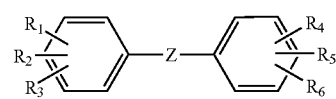

wherein, $R^1$ is chosen from hydroxyl and amino groups optionally substituted with a group chosen from $C_{1-4}$ alkyl, $C_{1-4}$ hydroxyalkyl and ($C_{1-4}$ alkoxy)($C_{1-4}$ alkyl), $R^2$, $R^3$, $R^4$, $R^5$ and $R^6$, which may be identical or different, are chosen from a hydrogen atom, hydroxyl groups, and amino groups, optionally substituted with at least one group chosen from $C_{1-4}$ alkyl, $C_{1-4}$ hydroxyalkyl and ($C_{1-4}$ alkoxy) ($C_{1-4}$ alkyl) groups, and from carboxylic groups and sulphonic acid groups, Z is chosen from a direct bond, a saturated and unsaturated, optionally hydroxylated $C_{1-4}$ hydrocarbon-based chain, carbonyl, sulphonyl and imino groups, an oxygen atom, a sulphur atom, and a group of formula Q—($CH_2$—P—$CH_2$—Q')$_o$ wherein P is chosen from a direct bond, a —$CH_2$— group, a —CHOH— group, Q and Q', which may be identical or different, are each chosen from an oxygen atom, a group $NR^7$, wherein $R^7$ is chosen from a hydrogen atom, a $C_{1-4}$ alkyl group and $C_{1-4}$ hydroxyalkyl group, and a group chosen from O—($CH_2$)$_p$NH and NH—($CH_2$)$_p$'—O, wherein p and p' are equal to 2 or 3 and o is a number ranging from 1 to 4.

The non-aromatic primary or secondary amines are chosen from, for example, 2-aminoethanol, 2-methoxyethylamine, 2-ethoxyethylamine, 2-(2-aminoethoxy)ethanol, 2-aminopropanol, 3-aminopropanol, 2,3-dihydroxypropylamine, 4-hydroxypropylamine, 2-aminopropane-1,3-diol, 2-amino-2-methylpropanol, 2-amino-2-methylpropane-1,3-diol, 2-amino-2-hydroxymethylpropane-1,3-diol, tetrahydropentylamine, pentahydroxyhexylamines such as glucamine, D-glucosamine, D-galactosamine, 1,2-diaminoethane, 1,2- or 1,3-diaminopropane, 1,3-diamino-2-propanol, 2-(2-aminoethylamino)ethylamine, 2-(2-aminoethylamino)ethanol, 3-(2-aminoethylamino)propylamine, and 3-(2-aminoethylamino)propanol.

The compounds comprising an activated methylene function are chosen, for example, from the following: 1,2,3,3-tetramethyl-3H-indolium iodide, 1,2,3,3-tetramethyl-3H-indolium p-toluenesulfonate,1,2,3,3-tetramethyl-3H-indolium methanesulphonate, 1,3,3-trimethyl-2-methyleneindoline, 2,3-dimethylbenzothiazolium iodide, 2,3-dimethylbenzothiazolium p-toluenesulphonate, rhodanine, rhodanine-3-acetic acid, 1-ethyl-2-quinaldinium iodide, 1-methyl-2-quinaldinium iodide, barbituric acid, thiobarbituric acid, 1,3-dimethylthiobarbituric acid, diethylthiobarbituric acid, oxindole, 3-indoxyl acetate, coumarone and 1-methyl-3-phenyl-2-pyrazolinone.

These primary and secondary amines and these compounds comprising activated methylene functions, and also other compounds comprising labile hydrogen, are further described in patent applications German Patent Nos. DE 43 17 855, DE 197 17 222, DE 198 45 481 and DE 197 45 355, in which they are used for dyeing keratin fibers in combination with compounds other than the ninhydrin compounds of formula (I).

When the ninhydrin compounds of formula (I) are used in combination with a primary or secondary amine or with a compound comprising an activated methylene function, may be beneficial for these various reagents to be stored separately in order to avoid a premature colored reaction. The reagents are thus placed in contact only immediately before application to the hair, by extemporaneous mixing of two compositions comprising, respectively, the ninhydrin compounds and the compounds comprising labile hydrogen. The reagents may also be placed in contact directly on the hair by successive application of the various reagents.

Thus, one aspect described herein is related to a multi-component hair coloring agent comprising
- as a first component, a composition (a) comprising at least one ninhydrin compound of formula (I), and
- as a second component, a composition (b) comprising at least one compound comprising a primary or secondary amine function or at least one compound comprising an activated methylene function, as described above.

This multi-component hair coloring agent may be in a multi-compartment kit, with at least one first compartment containing the first component (composition (a)) and at least one second compartment containing the second component (composition (b)).

Another aspect described herein is related to a cosmetic dye composition comprising at least one ninhydrin compound of formula (I) and at least one cosmetic active principle.

The cosmetic active principles present in the cosmetic compositions disclosed herein are chosen, for example, from vitamins, saccharides, oligosaccharides, hydrolyzed and non-hydrolyzed, modified and unmodified polysaccharides, amino acids, oligopeptides, peptides, hydrolyzed and non-hydrolyzed, modified and unmodified proteins, polyamino acids, enzymes, branched and unbranched fatty acids and fatty alcohols, animal, plant and mineral waxes, ceramides and pseudoceramides, hydroxylated organic acids, UV-screening agents, antioxidants, free-radical scavengers, chelating agents, antidandruff agents, seborrhoea regulators, calmatives, cationic, anionic, nonionic and amphoteric surfactants, cationic, anionic, neutral and amphoteric polymers, organomodified and non-organomodified silicones, mineral, plant and animal oils, polyisobutenes, and poly($\alpha$-olefins), fatty esters, anionic polymers in dissolved and dispersed form, nonionic polymers in dissolved and dispersed form, reducing agents, solvents, hair dyes such as direct dyes and oxidation dye precursors (bases and couplers) other than the claimed compounds comprising a primary or secondary amine function, oxidizing agents such as hydrogen peroxide optionally combined with persalts, and pigments.

In one embodiment, the cosmetic active principle may be present in a proportion ranging from 0.001% to 50% by weight, such as from 0.01% to 20% by weight and from 0.1% to 10% by weight relative to the total weight of the cosmetic composition.

In one embodiment of the cosmetic dye composition disclosed herein, the cosmetic active principle comprises at least one ingredient chosen from surfactant and polymer agents, these agents possibly being of nonionic, cationic, anionic or amphoteric nature.

The hair dye compositions disclosed herein are stable on storage when they contain, as sole reagents, ninhydrin compounds of formula (I). However, when they contain both ninhydrin compounds of formula (I) and compounds comprising labile hydrogen, such as primary or secondary amines or compounds comprising an activated methylene function, these compositions typically are used immediately after mixing the composition comprising the ninhydrin compounds of formula (I) with that comprising compound(s) comprising labile hydrogen.

These ready-to-use dye compositions, whether they are stable on storage or prepared immediately before use, generally have a pH ranging from 2 to 12, such as from 3 to 11.

In one embodiment, the content of ninhydrin compounds of formula (I) ranges from 0.0001% to 30% by weight relative to the total weight of the composition.

The compounds comprising labile hydrogen used in combination with the ninhydrin compounds of formula (I) may be present in a proportion ranging from 0.0001% to 30% by weight relative to the total weight of the composition.

Another aspect disclosed herein relates to a hair dyeing process comprising applying to the hair a ready-to-use hair dye composition as described above. This composition is left in contact with the hair fibers for a time that is sufficient to obtain the desired coloration. This leave-in time generally ranges from 5 minutes to 1 hour, such as from 15 to 30 minutes. The color reaction between the ninhydrin compounds and the amine functions of the keratin or the compounds comprising labile hydrogen that are optionally present may be accelerated by heating the hair impregnated with the dye composition. The heating temperature generally does not exceed 80° C., such as less than or equal to 60° C.

After obtaining the desired coloration, the hair is rinsed and washed.

When compounds comprising labile hydrogen such as primary or secondary amines or compounds comprising an activated methylene function are used, the application of the reagents participating in the color reaction may also take place in two stages. For example, two different compositions comprising, respectively, at least one ninhydrin compound of formula (I) and at least one compound comprising a primary or secondary amine function or an activated methylene function may be applied successively.

Also disclosed herein is a two-stage dyeing process comprising applying to the hair one after the other, in any order, a composition (a) and a composition (b) as defined above for the multi-component coloring agent.

This separate application of two reactive compositions has at least one advantage of avoiding the handling of colored compositions and thus reducing the risks of soiling materials such as clothing.

Satisfactory hair colorations can also be obtained when an intermediate rinsing step is inserted between the application of the first composition and the application of the second composition.

Analogously with that described above, the hair impregnated with composition (a) and/or (b) may be heated, such as up to a temperature of 80° C. In one embodiment, the hair may be heated up to a temperature not exceeding 60° C., such heating making it possible to accelerate the color reaction and to shorten the leave-in time.

EXAMPLE

The following composition was prepared:

| | |
|---|---|
| Naphto Ninhydrine (*) | $10^{-2}$ moles |
| Ethanol | 50 g |
| NaOH | qs pH 7 |
| Distilled water | qsp 100 g |

(*) naphto ninhydrine:

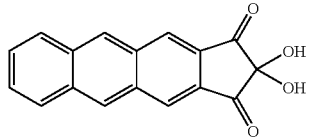

This composition was applied to two locks of natural and permanently waved hair which were 90% white, of 1 g each. The bath ratio was 5, the leave-in time 30 minutes and the temperature 60° C. At the end of the leave-in time, the locks were rinsed and then washed with a standard shampoo.

The obtained locks were colored with golden highlights.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

What is claimed is:

1. A process for dyeing keratin material comprising:
applying to the keratin material a composition comprising, in a medium that is suitable for dyeing, at least one compound of formula (I):

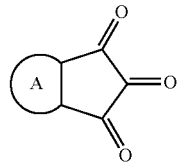

wherein A comprises an at least 12-membered fused aromatic polycycle.

2. The process according to claim 1, wherein the group A is chosen from anthracenyl, tetracenyl, phenanthrenyl and azulenyl groups.

3. The process according to claim 1, wherein the group A is substituted with one or more groups chosen from halo groups, $C_1$–$C_6$ alkyl groups, hydroxyl groups, $C_1$–$C_6$ alkoxy groups, amino groups, imidazolyl groups, pyridyl groups, mono- and di($C_1$–$C_6$ alkyl)amino groups, mono- and dihydroxy($C_1$–$C_6$ alkyl)amino groups, tri($C_1$–$C_6$ alkyl)ammonio groups, thio groups, ($C_1$–$C_6$ alkyl)thio groups, thio($C_1$–$C_6$ alkyl)groups, ($C_1$–$C_6$ alkyl)carbonyl groups, hydrogenocarbonyl groups, hydroxycarbonyl groups, ($C_1$–$C_6$ alkoxy)carbonyl groups, nitro groups and sulphonato groups, and the corresponding protonated groups.

4. The process according to claim 3, wherein the corresponding protonated groups are chosen from ammonio, imidazolio and pyridinio groups.

5. The process according to claim 1, wherein said composition further comprises at least one activator that makes it possible to modify the reaction kinetics of the ninhydrin compound with the keratin material.

6. The process according to claim 5, wherein the at least one activator is chosen from oxidizing agents, reducing agents, Brönsted acids, metal catalysts, proteins, compounds that modify the ionic strength of the medium, compounds comprising labile hydrogen chosen from compounds comprising a primary or secondary amine function and those comprising an activated methylene function.

7. The process according to claim 6, wherein the at least one activator is chosen from compounds comprising a primary or secondary amine function and those comprising an activated methylene function.

8. The process according to claim 7, wherein the compound comprising a primary or secondary amine function comprises an aromatic amine chosen from:

N,N-dimethyl-p-phenylenediamine, N,N-diethyl-p-phenylenediamine, N-(2-hydroxyethyl)-N-ethyl-p-phenylenediamine, N,N,-bis(2-hydroxyethyl)-p-phenylenediamine, N-(2-methoxyethyl)-p-phenylenediamine, 2,3-, 2,4- and 2,5-dichloro-p-phenylenediamine, 2-chloro-p-phenylenediamine, 2,5-dihydroxy-4-morpholinoaniline dihydrobromide, 2-, 3-and 4-aminophenol, 2-aminomethyl-4-aminophenol, 2-hydroxymethyl-4-aminophenol, ortho-phenylenediamine, p-phenylenediamine, ortho-toluenediamine, 2,5-diaminotoluene, 2,5-diaminophenol, 2,5-diaminophenethol, 4-amino-3-methylphenol, 2-(2,5-diamino -phenyl)ethanol, 2,4-diaminophenoxyethanol, 2-(2,5-diaminophenoxy)ethanol, 4-methylaminoaniline, 3-amino-4-(2'-hydroxyethyloxy)aniline, 3,4-methylenediaminoaniline, 3,4-methylenedioxyaniline, 3-amino-2,4-dichlorophenol, 4-methylaminophenol, 2-methyl-5-aminophenol, 3-methyl-4-aminophenol, 2-methyl-5-(2-hydroxyethylamino)phenol, 6-methyl- 3-amino-2-chlorophenol, 2-methyl-5-amino-4-chlorophenol, 3,4-methylene-dioxyphenol, 5-(2-hydroxyethylamino)-4-methoxy-2-methylphenol, 4-amino-2-hydroxymethylphenol, 1,3-diamino-2,4-dimethoxybenzene, 2-, 3- and 4-aminobenzoic acid, 2-amino-, 3-amino- and 4-aminophenylacetic acid, 2,3-, 2,4-, 2,5-, 3,4- and 3,5-diaminobenzoic acid, 4-amino- and 5-aminosalicylic acid, 3-amino-4-hydroxybenzoic acid, 4-amino-3-hydroxybenzoic acid, 2-amino, 3-amino- and 4-aminobenzenesulphonic acid, 3-amino-4-hydroxybenzenesulphonic acid, 4-amino-3-hydroxynaphthalene-1-sulphonic acid, 6-amino-7-hydroxynaphthalene-2-sulphonic acid, 7-amino-4-hydroxynaphthalene-2-sulphonic acid, 4-amino-5-hydroxynaphthalene-2,7-disulphonic acid, 3-amino-2-naphthoic acid, 3-aminophthalic acid, 5-aminoisophthalic acid, 1,3,5-triaminobenzene, 1,2,4-triaminobenzene, 1,2,4,5-tetraaminobenzene, 2,4,5-triaminophenol, pentaaminobenzene, hexaaminobenzene, 2,4,6-triaminoresorcinol, 4,5-diaminopyrocatechol, 4,6-diaminopyrogallol, 3,5-diamino-4-hydroxypyrocatechol, and aromatic anilines and aromatic phenols comprising another aromatic residue, of formula (II) below

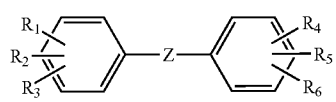

wherein

R$^1$ is chosen from hydroxyl and amino groups optionally substituted with a group chosen from C$_{1-4}$ alkyl, C$_{1-4}$ hydroxyalkyl and (C$_{1-4}$ alkoxy)(C$_{1-4}$ alkyl) groups, R$^2$, R$^3$, R$^4$, R$^5$ and R$^6$, which may be identical or different, are each chosen from a hydrogen atom, hydroxyl groups and amino groups, optionally substituted with a group chosen from C$_{1-4}$ alkyl, C$_{1-4}$ hydroxyalkyl and (C$_{1-4}$ alkoxy)(C$_{1-4}$ alkyl), and from carboxylic groups and sulphonic acid groups, Z is chosen from a direct bond, saturated and unsaturated, optionally hydroxylated C$_{1-4}$ hydrocarbon-based chains, carbonyl, sulphonyl, and imino groups, an oxygen atom, a sulphur atom, and a group of formula Q—(CH$_2$—P—CH$_2$—Q')$_o$ wherein P is chosen from a direct bond, a —CH$_2$— group, and a —CHOH—) group, Q and Q', which may be identical or different, are each chosen from an oxygen atom, a group NR$^7$, wherein R$^7$ is chosen from a hydrogen atom, a C$_{1-4}$ alkyl group, a C$_{1-4}$ hydroxyalkyl group, and a group chosen from O—(CH$_2$)$_p$NH and NH—(CH$_2$)$_{p'}$—O, wherein p and p' are equal to 2 or 3 and o is a number ranging from 1 to 4, and an aliphatic amine chosen from 2-aminoethanol, 2-methoxyethylamine, 2-ethoxyethylamine, 2-(2-aminoethoxy)ethanol, 2- and 3-aminopropanol, 2,3-dihydroxypropylamine, 4-hydroxypropylamine, 2-aminopropane-1,3-diol, 2-amino-2-methyl-propanol, 2-amino-2-methylpropane-1,3-diol, 2-amino-2-hydroxymethylpropane-1,3-diol, tetrahydropentylamine, pentahydroxyhexylamines, glucamine, D-glucosamine, D-galactosamine, 1,2-diaminoethane, 1,2- and 1,3-diaminopropane, 1,3-diamino-2-propanol, 2-(2-aminoethylamino)ethylamine, 2-(2-aminoethylamino)ethanol, 3-(2-aminoethylamino)propylamine, and 3-(2-aminoethylamino)propanol.

9. The process according to claim 7, wherein the compound comprising an activated methylene function is chosen from 1,2,3,3-tetramethyl-3H-indolium iodide, 1,2,3,3-tetramethyl-3H-indolium p-toluenesulphonate, 1,2,3,3-tetramethyl-3H-indolium methanesulphonate, 1,3,3-trimethyl-2-methyleneindoline, 2,3-dimethylbenzothiazolium iodide, 2,3-dimethylbenzothiazolium p-toluenesulphonate, rhodanine, rhodanine-3-acetic acid, 1-ethyl-2-quinaldinium iodide, 1-methyl-2-quinaldinium iodide, barbituric acid, thiobarbituric acid, 1,3-dimethylthiobarbituric acid, diethylthiobarbituric acid, oxindole, 3-indoxyl acetate, coumarone, and 1-methyl-3-phenyl-2-pyrazolinone.

10. The process according to claim 1, wherein the composition has a pH ranging from 2 to 12.

11. The process according to claim 10, wherein the composition has a pH ranging from 3 to 11.

12. The process according to claim 1, wherein the concentration of the compound of formula (I) ranges from 0.0001% to 30% relative to the total weight of the composition.

13. The process according to claim 7, wherein the concentration of the compound comprising an activated methylene function or of the compound comprising a primary or secondary amine function ranges from 0.0001% to 30% relative to the total weight of the composition.

14. A cosmetic dyeing composition comprising, in a medium that is suitable for dyeing, keratin fibers, at least one ninhydrin compound of formula (I):

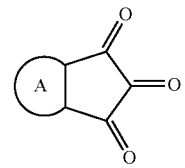

wherein A comprises an at least 12-membered fused aromatic polycycle, and at least one ingredient chosen from nonionic, cationic, anionic, and amphoteric surfactants and from nonionic, cationic, anionic, and amphoteric polymers.

15. A ready-to-use cosmetic composition comprising at least one ninhydrin compound of formula (I):

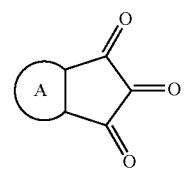

wherein A comprises an at least 12-membered fused aromatic polycycle, at least one ingredient chosen from nonionic, cationic, anionic, and amphoteric surfactants and from nonionic, cationic, anionic, and amphoteric polymers, and at least one compound chosen from compounds comprising a primary or secondary amine function and compounds comprising an activated methylene function, wherein the ready-to-use composition is prepared at the time of use.

16. A multi-component coloring agent for keratin material comprising:

a first component (a) comprising at least one ninhydrin compound of formula (I):

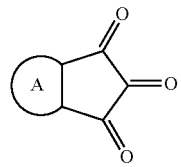
(I)

wherein A comprises an at least 12-membered fused aromatic polycycle, and a second component (b) comprising at least one activator which makes it possible to modify the reaction kinetics of the ninhydrin compound of formula (I) with the keratin material.

17. A multi-compartment kit for coloring keratin material comprising:

at least one first compartment comprising at least one ninhydrin compound of formula (I):

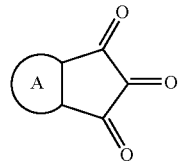
(I)

wherein A comprises an at least 12-membered fused aromatic polycycle, and at least one second compartment comprising at least one activator which makes it possible to modify the reaction kinetics of the ninhydrin compound of formula (I) with the keratin material.

18. A process for dyeing hair comprising:

applying to the hair a composition comprising, in a medium that is suitable for dyeing, at least one ninhydrin compound chosen from compounds of formula (I):

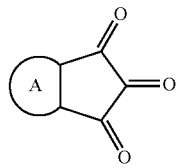
(I)

wherein A comprises an at least 12-membered fused aromatic polycycle, leaving the composition on the hair for a time sufficient to obtain a desired coloration, and rinsing and washing the hair.

19. The process according to claim 18, further comprising heating the hair impregnated with hair dye composition up to a temperature of 80° C.

20. The process according to claim 19, wherein the hair is heated to a temperature of 60° C.

21. A process for dyeing hair comprising:

applying to the hair a first composition (a) comprising at least one ninhydrin compound of formula (I):

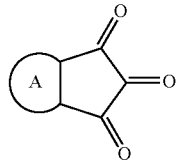
(I)

wherein A comprises an at least 12-membered fused aromatic polycycle, and a second composition (b) comprising at least one activator which makes it possible to modify the reaction kinetics of the ninhydrin compound of formula (I) with the hair, wherein the first composition (a) and the second composition (b) are applied in any order.

22. The process according to claim 21, wherein an intermediate rinsing step is inserted between the application of composition (a) and the application of composition (b).

23. The process according to claim 21, further comprising heating the hair impregnated with at least one composition (a) and/or the at least one composition (b) to a temperature up to 80° C.

24. The process according to claim 22, wherein the hair is heated up to a temperature of 60° C.

* * * * *

UNITED STATES PATENT AND TRADEMARK OFFICE
CERTIFICATE OF CORRECTION

| | | |
|---|---|---|
| PATENT NO. | : 7,179,305 B2 | Page 1 of 1 |
| APPLICATION NO. | : 10/898368 | |
| DATED | : February 20, 2007 | |
| INVENTOR(S) | : Grégory Plos and Luc Gourlaouen | |

It is certified that error appears in the above-identified patent and that said Letters Patent is hereby corrected as shown below:

In claim 8, column 8, line 56, "3-and" should read --3- and--.

In claim 8, column 9, line 2, "3,4-methylene -dioxyphanol," should read --3,4-methylene-dioxyphenol,--.

In claim 8, column 9, line 50, "-CHOH-)" should read -- -CHOH- --.

Signed and Sealed this

Seventeenth Day of April, 2007

JON W. DUDAS
*Director of the United States Patent and Trademark Office*